United States Patent
Bongiovanni et al.

[11] Patent Number: 5,950,625
[45] Date of Patent: Sep. 14, 1999

[54] ISOLATION BAG

[75] Inventors: Richard Anthony Bongiovanni, Santa Ana; Peter Andrew Barnett, Costa Mesa; Douglas Ellwood Shultz, Brea, all of Calif.

[73] Assignee: Northrop Grumman Corporation, Los Angeles, Calif.

[21] Appl. No.: 08/987,429

[22] Filed: Dec. 9, 1997

[51] Int. Cl.⁶ .................................................. A61G 15/00
[52] U.S. Cl. ............................ 128/845; 128/846; 600/21
[58] Field of Search .................................... 128/845, 846, 128/849–856; 600/21

[56] References Cited

U.S. PATENT DOCUMENTS

| | | | |
|---|---|---|---|
| 2,401,230 | 5/1946 | Colley | 128/845 |
| 3,875,927 | 4/1975 | Trexler | 60/21 |
| 4,275,719 | 6/1981 | Mayer | 128/849 |
| 4,367,728 | 1/1983 | Mutke | 600/21 |
| 4,485,806 | 12/1984 | Akers | 600/21 |

*Primary Examiner*—Michael A. Brown
*Attorney, Agent, or Firm*—Terry J. Anderson; Karl J. Hoch, Jr.

[57] ABSTRACT

An isolation bag for isolating a casualty from a contaminated environment. The bag is preferably fabricated from a transparent, biochemically resistive material and is specifically designed and configured to be utilized in combination with a self-contained transportable life support system. The isolation bag is further provided with a plurality of tubular passages which are designed to be filled with air provided by the transportable life support system to thus cause the isolation bag to expand and form a semi-rigid structure. A multiplicity of apertures are formed upon the tubular passages in such a manner that enables refreshed air to pass therethrough which washes over the patient in a head-to-toe direction such that rapid removal of toxic and infectious residues is facilitated.

15 Claims, 2 Drawing Sheets

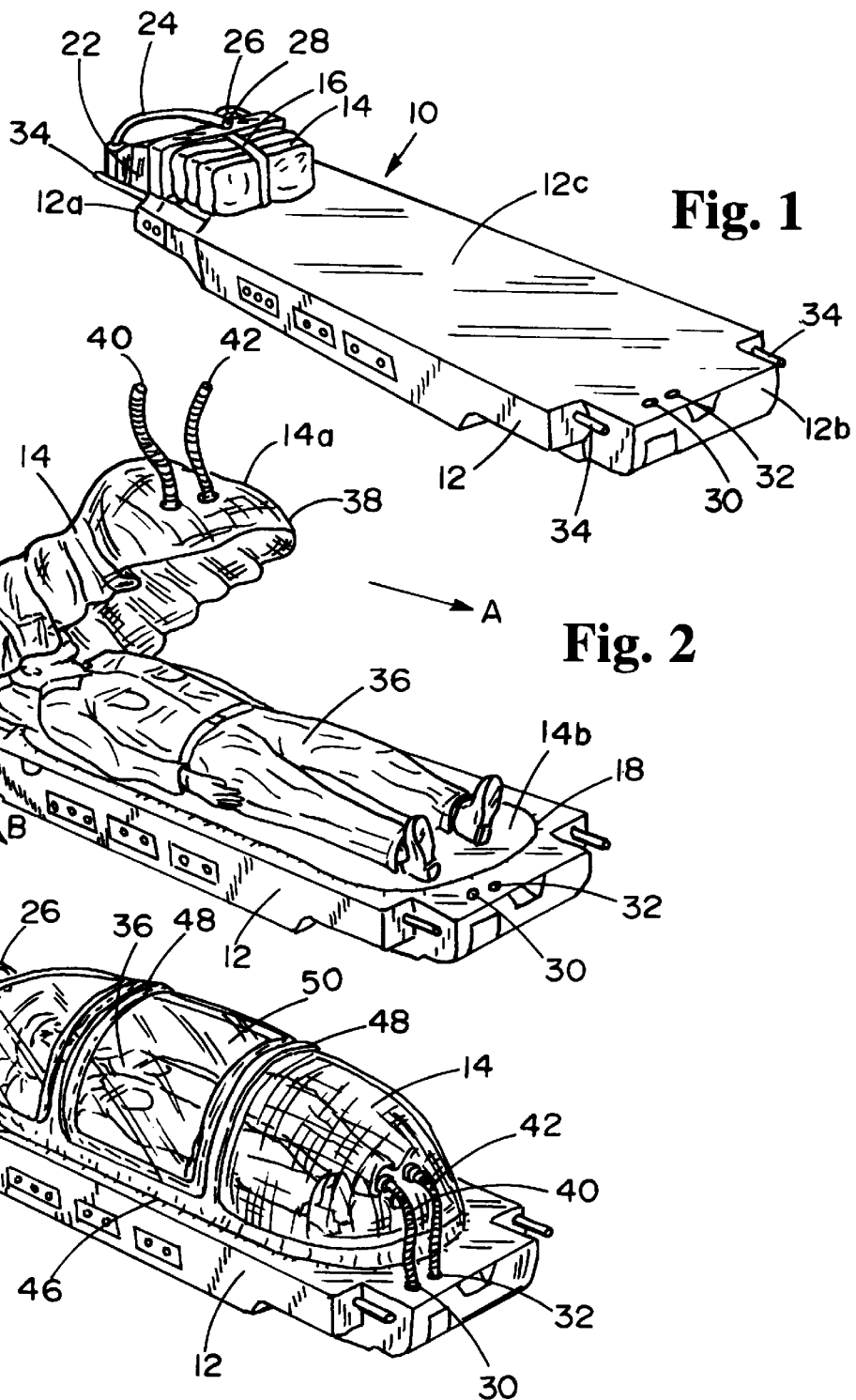

ISOLATION BAG

FIELD OF THE INVENTION

The present invention relates generally to medical devices utilized to isolate and treat intensive care patients outside of a medical facility, and more particularly, to a self-contained, transportable isolation bag utilized in the resuscitation, stabilization, and transport of medical patients that further facilitates the removal of toxic residues therefrom.

BACKGROUND OF THE INVENTION

Typically, when a person is injured and becomes a casualty in a contaminated environment, such as occurs in a chemical warfare confrontation, the casualty is placed within a litter bag or other type of enclosure for transportation to a medical facility. Ideally, the enclosure is manufactured of a material that inhibits or prevents the transfer of contaminants from the ambient environment to the casualty.

In many cases, it is imperative that medical treatment be given to the casualty immediately. However, in order to administer treatment, the casualty must first be isolated and transported into an enclosure within which medical personnel may work on the casualty or additional means must be provided for allowing access to the casualty without introducing contaminants into the enclosure containing the casualty. In this regard, it is desirable to isolate the patient from the environment when the environment contains substances which may be detrimental to the medical patient. For example, if the patient has suffered severe blood loss or is experiencing difficulty breathing, then it is desirable to prevent the patient from breathing dust, engine exhaust, smoke, etc. It is also desirable to isolate the medical patient from the environment when bacteriological, chemical and/or radiological hazards are present, as may occur during battlefield conditions.

In addition, it would be advantageous if such isolated environment were caused to facilitate the removal of such toxic and infectious residues that may be present on the clothing and/or skin of such isolated medical patient to thus enable the patient to become further stabilized during transit to a suitable medical facility. Ideally, the isolated medical patient would be contained within an environment that is provided with air that is constantly recycled, decontaminated and refreshed such that such toxic and infectious residues are rapidly removed from the isolated medical patient.

Unfortunately, prior art apparatuses currently available for treating the casualty in the field are generally ineffective in providing an environment conducive to the administration of medical treatment, and can thus cause treatment to be delayed until the casualty is transported to an adequate medical facility, which is frequently not readily accessible. Such prior art apparatuses are further generally deficient in providing an environment where the casualty is protected from contaminants, let alone actually facilitate the removal of contaminants already present on the skin and/or clothes of the casualty.

As such, there is a need in the art for an isolation system, and in particular an isolation bag within which a medical patient is placed at the battlefield and within which the medical patient remains until a suitable medical facility can be accessed. It is further desirable to provide an isolation system having an isolation bag wherein the latter can protect a medical patient contained therewithin from an contaminated external environment such that the condition of such patient is not made worse by the ingress of poisonous substances resulting from chemical and/or biological attack, as well as other harsh and extreme weather conditions arising from rain, wind, dust, hot, cold, wet and dry climatic conditions. There is still further a need for an isolation bag as part of an isolation system that is capable of delivering a constant supply of air to a patient contained therewithin wherein such air is constantly recycled, decontaminated and refreshed and that is further capable of delivering such air in a manner such that toxic and infectious residues present upon the patient may be rapidly removed, filtered and decontaminated. There is additionally a need for such an isolation bag that, as part of a medical patient isolation system, is specifically designed and configured to occupy a small space and can be easily transported when collapsed, but may be rapidly and easily expanded for use.

SUMMARY OF THE INVENTION

The present invention specifically addresses and alleviates the above-mentioned deficiencies associated with the prior art. More particularly, the present invention comprises an isolation bag for use with a transportable litter having a self-contained life support system integrated therein for protecting a casualty or medical patient from an external contaminated environment. The isolation bag is further capable of delivering a constant supply of recycled, decontaminated and refreshed air that facilitates the removal of toxic infectious residues present upon the patient contained therein.

According to a preferred embodiment, the bag comprises a covering positionable about a casualty or medical patient when the latter assumes a supine position upon the litter with which the isolation bag is used. The isolation bag comprises the combination of a first lower bag portion and a second upper bag portion that are designed and configured to mate with one another and form an air-tight chamber within which a patient may be positioned. The entrance to such chamber is through a long zippered opening formed about the peripheral edges of the first and second bag portions that is specifically configured to form an anti-leak seal when closed. Formed about the upper bag portion are a series of tubular gas passages designed and configured to receive pressurized gas from an external source such that when the tubular gas passages are filled with a pressurized gas, the upper bag portion assumes a semi-rigid, parallel piped structure.

Formed upon the interior of such tubular passageways are a plurality of apertures oriented to deliver a constant stream of air to the patient contained therewithin. In a preferred embodiment, the plurality of apertures are so formed upon the tubular structures of the cover such that as air is delivered, it is washed over the patient in a head-to-toe direction such that rapid removal of toxic and infectious residues is facilitated. To facilitate the passage of air through the chamber in such a manner, there is formed upon one end of the bag an outlet or exhaust valve designed to draw air delivered into the bag out therefrom in a proximal to distal direction.

The isolation bag is preferably fabricated from chemical and/or biochemical resistive materials that are further capable of protecting a patient contained within the bag from harsh and extreme weather conditions arising from rain, wind, dust, hot, cold, wet and dry climatic conditions. The isolation bag is further preferably fabricated from a transparent material to enable the patient contained therewithin to be viewed by medical personnel, as well as to minimize patient claustrophobic experiences. To facilitate medical treatment, the isolation bag is preferably provided with patient access means, preferably in the form of a flexible hand sock-type portal mounted upon the isolation bag that is strategically positioned for complete patient access. Ideally, such portal system is designed to be left hand/right hand independent and designed to maximize the provider's hand manipulative abilities and finger functioning dexterity. Such isolation bag is further preferably configured to assume a small, compact space when collapsed so that the same may be easily stored and transported, but may be readily deployed when necessary to form a closure about a patient.

It is therefore an object of the present invention to provide an isolation bag for protecting a patient from a toxic or infectious environment that further protects the patient against harsh and extreme weather conditions arising from rain, wind, dust, hot, cold, wet and dry climatic conditions.

Another object of the present invention is to provide an isolation bag as part of an isolation system for protecting a patient from a toxic or infectious environment that is capable of interfacing with conventional transportable life support system equipment, and more particularly the air supply and ventilator componentry thereof such that air supplied to the bag is delivered to and washed about the person contained therein.

Another object of the present invention is to provide an isolation bag as part of an isolation system for protecting a patient from a toxic or infectious environment that facilitates the rapid removal of toxic and infectious residues present upon the person contained therein.

Another object of the present invention is to provide an isolation bag as part of an isolation system for protecting a patient from a toxic or infectious environment wherein such bag is capable of assuming a small, compact space when collapsed so that the same may be easily stored and transported, but may be rapidly and easily deployed during use.

Another object of the present invention is to provide an isolation bag as part of an isolation system for protecting a patient from a toxic or infectious environment that allows a patient contained therewithin to be viewed by medical personnel and allow such medical personnel to quickly and easily access the patient's body when contained and enclosed therein.

A still further object of the present invention is to provide an isolation bag as part of an isolation system for protecting a patient from a toxic or infectious environment wherein such bag is of simple construction, and may be easily and readily used.

BRIEF DESCRIPTION OF THE DRAWINGS

These, as well as other features of the present invention, will be more apparent from the following description and drawings. It is understood that changes in the specific structure shown and described may be made within the scope of the claims without departing from the spirit of the invention.

FIG. 1 is a perspective view of an isolation bag constructed in accordance with a preferred embodiment of the present invention shown in a pre-packaged, collapsed configuration in combination with a prior art litter having a self-contained transportable life support system contained therein;

FIG. 2 is a perspective view of a patient assuming a supine position upon the litter with the isolation bag of the present invention being deployed thereabout;

FIG. 3 is a perspective view of the patient of FIG. 2 fully contained within the isolation bag of the present invention;

DETAILED DESCRIPTION OF THE PREFERRED EMBODIMENT

Figure 4:
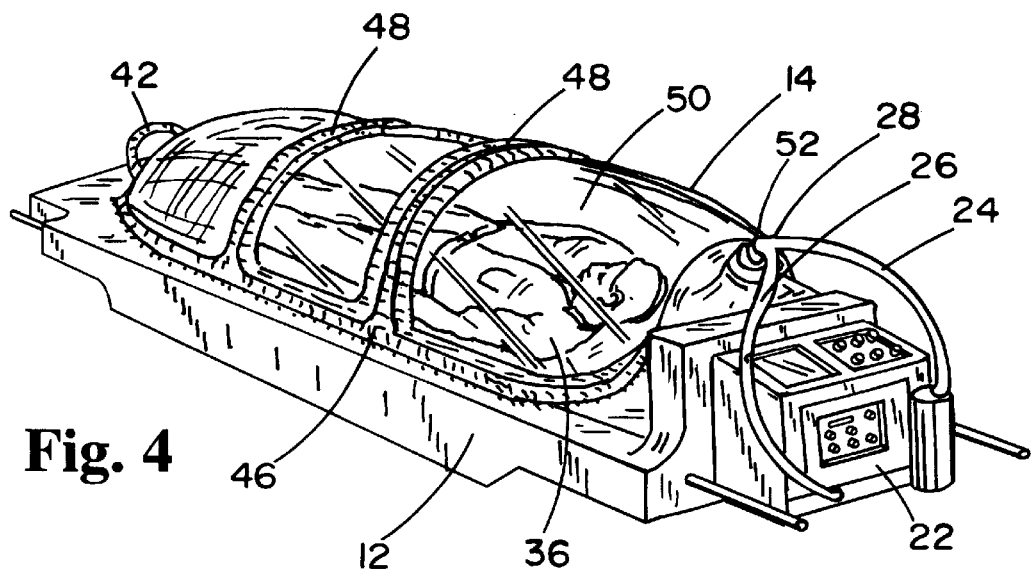
FIG. 4 is a rear perspective view of the patient, isolation bag, and life support system of FIG. 3, wherein there is further depicted a ventilator system shown coupled to said isolation bag.

The description set forth below in connection with the appended drawings is intended as a description of the presently preferred embodiment of the invention, and is not intended to represent the only form in which the present invention may be constructed or utilized. The description sets forth the functions and the sequence of steps for constructing and operating the invention in connection with the illustrated embodiment. It is to be understood, however, that the same or equivalent functions may be accomplished by different embodiments that are also intended to be encompassed within the spirit and scope of the invention.

Although discussed and illustrated herein as having particular application in battlefield situations, those skilled in the art will appreciate that the isolation bag of the present invention may be utilized in various different civilian applications, such as emergency rescue and medical evacuation, especially where the emission or production of poisonous gasses or particles contaminate the surrounding and where people in or close to the area of the emergency or catastrophe require immediate degassification and treatment. As such, the terms medical patient, patient and casualty as used herein are defined to include patients and/or victims of any accident and/or medical condition resulting in the need for emergency medical care.

Referring now to the drawings, and initially to FIG. 1, there is shown a self-contained isolation and environmental protection system 10 comprised of the combination of a litter 12 and an isolation bag 14 connectible therewith for the transportation of a patient from the field or a scene of an accident to a hospital. As is typical, the litter 12 is configured to have a proximal end 12a and a distal end 12b and an upper platform surface 12c upon which a medical patient may be placed, usually in a supine position.

The litter 12 may take the form of any of several systems well-known in the art that are provided with devices for monitoring and responding to the condition of the patient placed thereon, and will typically include devices for monitoring blood pressure, temperature, blood oxygen and heart rate. Exemplary of such litters include those self-contained transportable life support systems disclosed in co-pending U.S. patent application Ser. No. 08/667,693, the teachings of which are expressly incorporated therein by reference. Such litters 12 are of further advantage insofar as the same are typically designed and configured to fit within and be carried by a variety of military transport vehicles and aircraft such as UH-60 Blackhawk helicopter, the UH-1 Huey helicopter, the HMMWV, the C-130 winged aircraft and/or the C141 fixed wing aircraft. Such configuration is further compatible with standard NATO litter mounts such that the transportable life support system 10 of the present invention may simply be carried aboard such military evacuation vehicles in the same manner that a standard NATO stretcher having a battlefield casualty disposed thereupon is carried. To facilitate the transport of such litter 12, the same is typically provided with retention members 34 extending from the proximal and distal ends thereof.

Although not shown, typically incorporated into such litters 12 include ventilation systems designed to take air from the surroundings, extract contaminated particles and gas from the air by filtration, and force the resultant purified air to pass into an enclosure formed about the patient. The filtered air is typically mixed with air recycled from within the mobile unit or litter 12. As may be necessary, the air mixture is heated or cooled to a predetermined temperature and is then delivered into the mobile unit and subsequently removed and filtered so as to extract any remaining particles and gas.

Such ventilator systems are typically controlled via a control circuit 22 coupled therewith that is designed to regulate the operation of the ventilator, as well as other medical devices. A heater (not shown) is further preferably disposed within the litter 12 and in electrical communication with the control circuit 22 for providing heat to an interior portion or platform surface 12c of the litter 12 so as to maintain the interior portion above a predetermined minimum temperature. Similarly, a cooler is preferably disposed within the litter 12 and in electrical communication with the control circuit 22 for cooling an interior portion of the litter 12 so as to maintain the interior portion below a predetermined maximum temperature.

Mounted upon the litter 12 is an isolation bag 14 constructed in accordance to a preferred embodiment of the present invention. The isolation bag 14 is preferably designed and configured to assume a first collapsed, packaged configuration, as shown, and may be affixed to the litter 12 via strap 16. The isolation bag 14 is fabricated from those materials resistive to chemical and/or biological attack, namely, poisonous gasses or lethal bacterial used in the battlefield, or in the unintentional emission of poisonous substances. The isolation bag 14 is further fabricated from those materials well-known in the art that can withstand harsh and extreme weather conditions arising from rain, wind, dust, hot, cold, wet and dry climatic conditions. It will be further appreciated that such isolation bag 14 will preferably be fabricated from transparent materials so that in use, the patient 36 contained therein, depicted in FIGS. 3 and 4, may be visually observed by medical personnel. Additionally, by providing a transparent isolation bag 14, the patient 36 contained therein is less likely to experience a claustrophobic event insofar as such individual will be able to see his or her surroundings.

Referring now to FIG. 2, there is shown the isolation bag 14 as deployed over a casualty 36, the latter assuming a supine position upon the platform surface 12c of the litter 12. As illustrated, the isolation bag 14 is comprised of two parts, namely, a lower bag portion 14b and an upper bag portion 14a. Both bag portions 14a, 14b are extended from the proximal end 12a of the litter 12 in the direction indicated by the letter A. As will be appreciated, in order for the casualty 36 to assume such position within the isolation bag 14, it will first be necessary to extend the lower bag portion 14b upon the platform surface 12c with the upper bag portion 14a then being extended over the patient 36 toward the distal end of the litter to form a canopy over the patient 36.

In order for the upper and lower bag portions 14a, 14b to form an air-tight seal with one another, there is formed about the respective peripheral edges thereof respective sets of teeth 18, 38 that cooperate to form a leak-proof, zipper-like closure. In this respect, the isolation bag 14 is provided with a slide fastener 20 that, when advanced in the direction indicated by the letter B about the patient, causes the respective teeth 18, 38 to mate with one another and form the air-tight seal 44 shown in FIG. 3. The isolation bag 14 is additionally provided with exhaust tubes 40, 42 that are designed to interconnect with exhaust valves 30, 32 formed on the distal end 12b of the litter 12, discussed more fully below. The isolation bag 14 is further provided with a bezel 52, shown in FIG. 4, to which may be attached a nozzle 28 for interconnecting air inlet valves 24, 26 therewith. As will be recognized by those skilled in the art, air inlet valves 24, 26 are coupled with the control circuit 22 to thus enable the latter to direct the flow of air passing therethrough and into the isolation bag 14, discussed more fully below.

Referring now to FIG. 3, the isolation bag 14, and more particularly the upper bag portion 14a thereof, is shown in an inflated state. In this respect, horizontal peripheral edge 46 and ribs 48 extending therefrom are formed as tubular gas passages formed by flexible inner tubes fluidly connected to one another which are encased within the material of the upper bag portion 14a. Such material may be formed out of a flexible plastic material which may be either heat sealed or sewn around the tubular portions 46, 48, and is preferably formed of a material which is impermeable to any contaminates which are expected to be found in the environment in which the isolation bag 14 are to be used. In an alternative embodiment, the tubular gas passages 46, 48 are formed integrally with the upper bag portion 14a.

Figure 5:
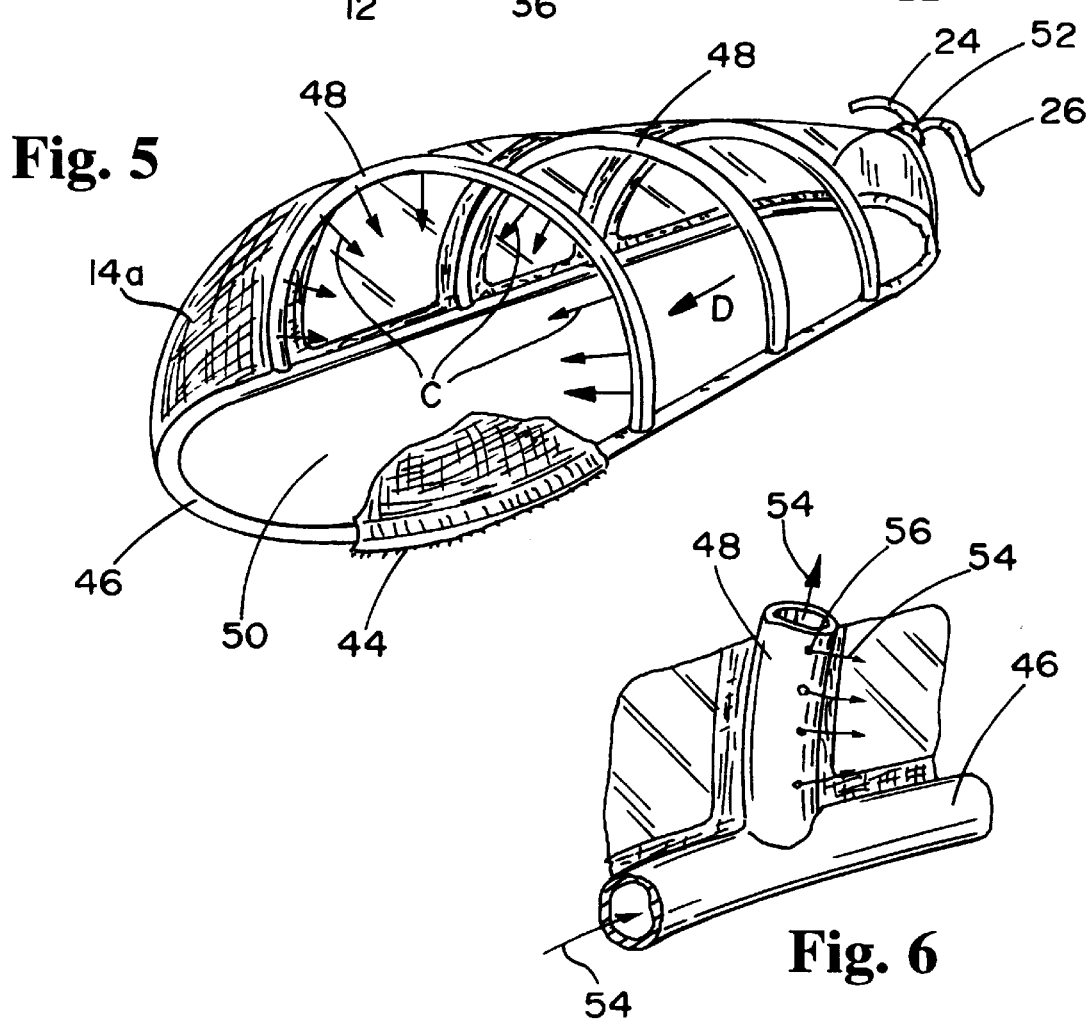
FIG. 5 is a perspective view of the isolation bag of the present invention indicating the flow of air delivered within the interior portion thereof as distributed by tubular gas passages formed thereon.

As illustrated in FIG. 5, air is provided from inlet valves 24, 26 and is caused to passed through the tubular passageways 46, 48 via a duct, which preferably takes the form of a bezel connection 52. As will be recognized by those skilled in the art, the gas passages 46, 48 are coupled to the bezel 52 in such a manner that air passing from inlet valves 24, 26 and through bezel connection 52 causes such passageways to become inflated to form a semi-rigid structure that defines a chamber or capsule 50 that isolates the medical patient 36. Either medical grade air, i.e., oxygen enriched air or oxygen, is provided via a ventilator (not shown) to the inlet valves 24, 26, and ultimately the patient 36. Such oxygen enriched air or oxygen may be provided to the ventilator either via the onboard oxygen generator system, pressurized oxygen bottles, or via an external source thereof. As discussed, there is further preferably contained within the litter 12 an environmental control system that, as those skilled in the art will appreciate, is comprised of a fan for drawing air into the upper litter, a filter for filtering the same from chemical, biological and radiological contaminants. There is further preferably provided in the air temperature controller that attemporates the air to a desired temperature as it is passed from the ventilator, through air delivery tubes 24, 26, through the passages 46, 48 and over the patient 36.

Figure 6:
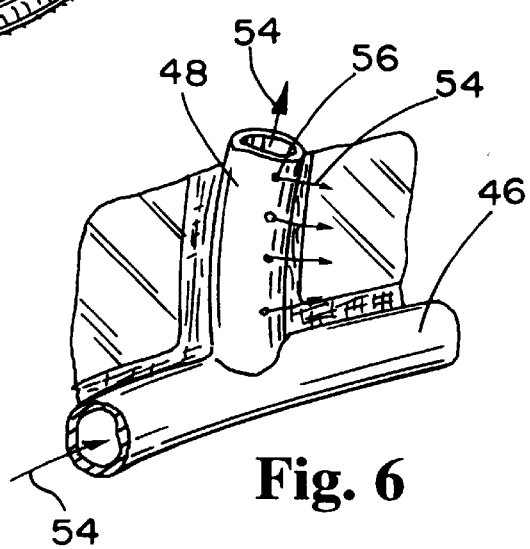
FIG. 6 is a perspective view of a portion of the tubular gas passageway formed upon the isolation bag of the present invention depicting a plurality of apertures through which is shown the direction of a flow of air.

The air is ultimately delivered radially inward about the chamber 50 defined by the inflated isolation bag 14, as indicated by the letter C. As shown in greater detail in FIG. 6, the path of air 54 that is passed about horizontal peripheral tubular passageway 46 flows upwardly through arcuate rib passageway 48 and eventually flows through apertures 56 formed thereon. As those skilled in the art will appreciate, such inward radial flow of air about the chamber 50 causes the patient contained therewithin to be thoroughly washed with such refreshed air.

Once the air has been washed about the patient 36, the same is removed via exhaust tubes 40, 42 formed on the distal end of upper bag portion 14a. Such tubes are connectable to exhaust valves 30, 32 formed on the distal end 12b of litter 12 that are coupled with a vacuum force to thus draw air from the proximal end of the isolation bag 14 to the distal end thereof, shown as the direction D in FIG. 5. By directing the air forced into the chamber 50 to be drawn from the proximal end to the distal end thus causes the same to wash over the patient in a head-to-toe flow direction. As those skilled in the art will appreciate, air washing over the contaminated patient in such a manner advantageously provides for rapid removal of toxic and infectious residues on clothing and skin which, once removed from the chamber 50 and into exhaust valves 30, 32, are filtered and decontaminated through an air recycle system contained within the litter 12 (not shown). Moreover, bathing the patient in air in such a manner eliminates dead air pockets which thus facilitates uniform heating, cooling and humidity control.

With respect to operation of the isolation bag 14 of the present invention, to the extent not already evident, such operation comprises the steps of removing the isolation bag 14 from its collapsed, packaged condition and attaching the bag bezel 52 to the ventilator nozzle 28, the latter being formed as part of a ventilator system contained within the litter 12. The lower bag portion 14b is then draped over the platform surface 12c of the litter 12 whereby the patient is then positioned thereupon. As will be recognized, to the extent additional medical devices, tubes, wiring and the like are to be deployed, the same are passed into the isolation bag opening and connected to the patient positioned thereupon.

Thereafter, the fastening device 20 is slid about the peripheral edges of the upper and lower bag portions to form an air-tight seal. Exhaust hoses 40, 42 are interconnected with the exhaust valves 30, 32 formed upon the litter. Environmental and decontamination systems contained within the litter 12 are then activated with air being passed from the ventilator contained within the litter 12, through passageways 24, 26 and bezel 52, and ultimately into the isolation bag 14.

Air will thus flow over the patient in the head-to-toe manner discussed above and will be removed via exhaust hoses 40, 42. While in such isolated state, the patient may be transported via conventional means and, upon arrival at a suitable medical facility, may be treated as necessary. To that end, the ventilator system need only be turned off and the sealable closure opened to thus gain access to the patient. Although not shown, the isolation bag 14 of the present invention may further be provided with patient access means, which may comprise a flexible hand sock-type portal which is formed upon the isolation bag 14 and strategically position for complete patient access. Such portal system, as those skilled in the art will appreciate, is preferably designed to be left hand/right hand independent and designed to maximize the care provider's hand manipulative abilities and finger functioning dexterity. Following use of the isolation bag 14, the same may be discarded or, alternatively, decontaminated, sterilized and repackaged for reuse.

Although the invention has been described herein with specific reference to a presently preferred embodiment thereof, it will be appreciated by those skilled in the art that various additions, modifications, deletions and alterations may be made to such preferred embodiment without departing from the spirit and scope of the invention. Accordingly, it is intended that all reasonably foreseeable additions, modifications, deletions and alterations be included within the scope of the invention as defined in the following claims.

What is claimed is:

1. A system for isolating a medical patient from a contaminated environment and facilitating the removal of contaminants from said patient comprising:

a) a flexible body capsule being formed from a material substantially impermeable to vapor fumes and contagions having an interior compartment;
b) a sealing apparatus formed upon said body capsule for opening and closing said body capsule and respectively exposing or isolating said interior compartment from said contaminated environment;
c) a source of contaminant-free pressurized air;
d) a duct formed upon said body capsule for coupling with said source of contaminant-free pressurized air;
e) a passageway formed upon said body capsule fluidly connected to said duct, said passageway having at least one inwardly facing aperture formed thereon such that when said passageway is supplied with said pressurized air, said air is caused to pass through said at least one aperture and into said interior compartment of said body capsule; and
f) an exhaust valve formed upon said interior compartment of said body capsule, said exhaust valve being so formed upon said interior of said body capsule such that in use, said exhaust valve causes said air delivered into said interior chamber from said at least one aperture to selectively wash over said medical patient and force said contaminant adhering to said patient to rapidly remove therefrom and exit from said interior compartment through said exhaust valve.

2. The apparatus of claim 1 wherein said body capsule is comprised of first and second bag portions interconnectible to one another that cooperate to form said interior compartment and said sealing apparatus comprises a fastener for fastening said first and second bag portions to one another.

3. The apparatus of claim 1 wherein said passageway for receiving pressurized air comprises a plurality of tubular gas passageways fluidly connected to one another such that when said plurality of tubular passageways are supplied with pressurized air, said body capsule assumes an expanded position to form a semi-rigid structure.

4. The apparatus of claim 1 wherein said passageway has a plurality of inwardly facing apertures formed thereon, said plurality of apertures being designed and configured to deliver and distribute air into said interior compartment of said body capsule.

5. The apparatus of claim 1 wherein said apparatus is designed and configured to assume a first collapsed configuration for facilitating the transport and storage thereof, and a second expanded configuration when in use.

6. The apparatus of claim 1 wherein said body capsule is sized and adapted to assume a first collapsed position and a second expanded position when said capsule is in use for providing access to said medical patient.

7. The apparatus of claim 1 wherein said body capsule is formed from a transparent material.

8. The apparatus of claim 1 wherein said body capsule has a window formed thereon to allow visual examination of said interior compartment from said external environment.

9. The apparatus of claim 1 wherein said body capsule is formed to have proximal and distal ends such that when said medical patient is contained within the interior compartment thereof, the head of said medical patient is oriented toward said proximal end and the feet and legs of said medical patient are oriented toward said distal end, said exhaust valve being formed upon said distal end of said body capsule such that when pressurized air is delivered to said interior compartment, said air is caused to selectively wash over said patient in a head-to-toe fashion.

10. A system for isolating a casualty from a contaminated environment and for facilitating the removal of toxic and infectious residues therefrom comprising:

a) a flexible body capsule of a material substantially impermeable to vapor fumes and contagions having an interior compartment and having proximal and distal ends that are sized and adapted to accommodate said medical patient's entire body;

b) a sealing apparatus formed upon said body capsule for opening and closing said body capsule and respectively exposing or isolating said interior compartment from said contaminated environment;

c) A source of pressurized air;

d) a duct formed upon said body capsule for interconnecting with and receiving pressurized air from said source of pressurized air;

e) at least one passageway formed upon said body capsule and having a plurality of inwardly-facing apertures formed thereon fluidly connected to said duct such that when pressurized air is received thereby, said air is delivered to said interior compartment; and f) an exhaust valve formed upon said body capsule and fluidly connected to said interior compartment thereof, said exhaust valve being selectively positioned such that when said air is delivered to said interior compartment, said air is caused to withdraw therefrom, said air being caused to withdraw from said interior compartment such that air flow is directed over said casualty and said toxic and infectious residues present thereupon are removed and expelled through said exhaust valve.

11. The apparatus of claim 10 wherein said passageway comprises a plurality of tubular gas passageways fluidly connected to one another such that when said tubular gas passageways are supplied with pressurized air, said interior chamber assumes an expanded configuration to form a semi-rigid structure.

12. The apparatus of claim 11 wherein said plurality of apertures are formed spaced about said tubular passageways such that when said pressurized air is delivered into said interior compartment, said air is caused to distribute evenly about the medical patient contained therewithin.

13. The apparatus of claim 10 wherein said apparatus is designed and configured to assume a first collapsed configuration for facilitating the transport and storage thereof, and a second expanded configuration when in use.

14. The apparatus of claim 10 wherein said apparatus is designed to be disposable following use thereof.

15. The apparatus of claim 10 wherein said apparatus is designed to be decontaminated and capable of being repackaged for reuse following the use thereof.

* * * * *